US009907835B2

(12) United States Patent
Nayar

(10) Patent No.: US 9,907,835 B2
(45) Date of Patent: Mar. 6, 2018

(54) STABLE FACTOR VIII FORMULATIONS WITH LOW SUGAR-GLYCINE

(71) Applicant: Advantech Bioscience Farmacêutica LTDA, Barueri (BR)

(72) Inventor: Rajiv Nayar, Danville, CA (US)

(73) Assignee: Advanced Bioscience Farmacêutica LTDA, San Paulo (BR)

( * ) Notice: Subject to any disclaimer, the term of this patent is extended or adjusted under 35 U.S.C. 154(b) by 0 days.

(21) Appl. No.: 15/120,264

(22) PCT Filed: Mar. 30, 2015

(86) PCT No.: PCT/BR2015/000044
§ 371 (c)(1),
(2) Date: Aug. 19, 2016

(87) PCT Pub. No.: WO2015/149143
PCT Pub. Date: Oct. 8, 2015

(65) Prior Publication Data
US 2017/0065683 A1  Mar. 9, 2017

Related U.S. Application Data

(60) Provisional application No. 61/973,281, filed on Apr. 1, 2014.

(51) Int. Cl.
| | |
|---|---|
| A61K 38/37 | (2006.01) |
| A61K 47/18 | (2017.01) |
| A61K 47/22 | (2006.01) |
| A61K 47/26 | (2006.01) |
| A61K 9/19 | (2006.01) |
| A61K 47/02 | (2006.01) |

(52) U.S. Cl.
CPC ............ *A61K 38/37* (2013.01); *A61K 9/19* (2013.01); *A61K 47/02* (2013.01); *A61K 47/183* (2013.01); *A61K 47/22* (2013.01); *A61K 47/26* (2013.01)

(58) Field of Classification Search
CPC .......... A61K 38/37; A61K 9/19; A61K 47/02; A61K 47/183; A61K 47/22; A61K 47/26
See application file for complete search history.

(56) References Cited

U.S. PATENT DOCUMENTS

| | | | |
|---|---|---|---|
| 5,733,873 | A | 3/1998 | Osterberg et al. |
| 5,763,401 | A | 6/1998 | Nayar |
| 5,874,408 | A | 2/1999 | Nayar |
| 6,171,825 | B1 | 1/2001 | Chan et al. |
| 6,599,724 | B1 | 7/2003 | Mikaelsson et al. |
| 6,780,614 | B2 | 8/2004 | Negrier et al. |
| 6,887,852 | B1 | 5/2005 | Paik et al. |
| 2003/0099618 | A1 | 5/2003 | Couto et al. |
| 2004/0229335 | A1 | 11/2004 | Zhang et al. |
| 2009/0035807 | A1 | 2/2009 | McCellan et al. |
| 2009/0263866 | A1 | 10/2009 | Wilson et al. |
| 2011/0039302 | A1 | 2/2011 | Kaufman et al. |
| 2011/0198286 | A1 | 8/2011 | Niazi |
| 2013/0184216 | A1 | 7/2013 | Besman et al. |
| 2014/0051832 | A1 | 2/2014 | Demasi et al. |
| 2017/0009269 | A1 | 1/2017 | Ozturk |
| 2017/0067013 | A1 | 3/2017 | Ozturk et al. |
| 2017/0080059 | A1 | 3/2017 | Nayar |

FOREIGN PATENT DOCUMENTS

| | | |
|---|---|---|
| CZ | 290342 B6 | 7/2002 |
| WO | 2011/012725 A1 | 2/2011 |
| WO | 2011/062926 A2 | 5/2011 |

OTHER PUBLICATIONS

International Preliminary Report on Patentability corresponding to International Patent Application No. PCT/BR2015/000044, dated Apr. 16, 2016.
International Search Report with Written Opinion corresponding to International Patent Application No. PCT/BR2015/000044, dated Oct. 7, 2015.
Dierickx (1986) "In vitro interaction of organic copper (II) compounds with soluble glutathione S-transferases from rat liver," Res. Commun. Chem. Pathol. Pharmacol. 51:285-288.
Kompala et al. (2005) "Optimization of High Cell Density Perfusion Bioreactors," In; Cell Culture Technology for Pharmaceutical and Cell-Based Therapies. Eds.: Ozturk et al. CRC Press. pp. 387-416.
Ohashi et al. (2001) "Perfusion Cell Culture in Disposable Bioreactors," In; The Proceedings of the 17th ESACT Meeting Tylösand, Sweden, Jun. 10-14, 2001. pp. 403-409.
Woodside et al. (1998) "Mammalian Cell Retention Devices for Stirred Perfusion Bioreactors," Cytotechnology. 28(1-3):163-175.
International Preliminary Report on Patentability corresponding to International Patent Application No. PCT/BR2015/000019, dated Mar. 9, 2016.
International Preliminary Report on Patentability corresponding to International Patent Application No. PCT/BR2015/000025, dated Apr. 19, 2016.

(Continued)

*Primary Examiner* — Julie Ha
*Assistant Examiner* — Li Ni Komatsu
(74) *Attorney, Agent, or Firm* — Lathrop Gage LLP; James H. Velema, Esq.

(57) ABSTRACT

The present invention provides a novel albumin-free preparation of Factor VIII has a high amount of salt and a low concentration of sugar and of glycine. The high salt provides stability and an elegant cake structure as the major crystalline component. The sugar and glycine provide a complex amorphous matrix together with some amorphous non-crystallized salt for stabilization of Factor VIII. This formulation is suitable for B-domain deleted Factor VIII that requires a high ionic strength environment for stability. The addition of low amount of glycine to the sucrose prevents the crystallization of salt. This results in an amorphous matrix comprising of glycine, sucrose, and salt. This amorphous matrix provides a stabilizing environment where Factor VIII is protected by three stabilizers; amino acid (glycine), sugar (sucrose or trehalose), and salt (NaCl). Such an amorphous matrix that can stabilize the Factor VIII across lyophilization and during storage as a lyophile.

19 Claims, 10 Drawing Sheets

(56) References Cited

OTHER PUBLICATIONS

International Preliminary Report on Patentability corresponding to International Patent Application No. PCT/BR2015/000045, dated Mar. 17, 2016.
International Search Report with Written Opinion corresponding to International Patent Application No. PCT/BR2015/000019, dated Oct. 7, 2015.
International Search Report with Written Opinion corresponding to International Patent Application No. PCT/BR2015/000025, dated Oct. 7, 2015.
International Search Report with Written Opinion corresponding to International Patent Application No. PCT/BR2015/000045, dated Oct. 6, 2015.

STABLE FACTOR VIII FORMULATIONS WITH LOW SUGAR-GLYCINE

CROSS-REFERENCE TO RELATED APPLICATIONS

This application is a 35 U.S.C. § 371 filing of international application number PCT/BR2015/000044, filed Mar. 30, 2015, which is based on and claims priority of U.S. provisional application No. 61/973,281 filed Apr. 1, 2014. The entire contents of which are incorporated herein by reference.

FIELD

This application relates generally to pharmaceutical formulations and particularly to lyophilized formulations for Factor VIII (FVIII) which is stabilized and with low amounts of sugar and glycine as protein stabilizers in a high ionic strength matrix, but without albumin (albumin free).

BACKGROUND

There are a number of albumin-free recombinant FVIII (rFVIII) formulations on the market using stabilization and formulation matrix excipients, such as sodium chloride, glycine, mannitol, sucrose, trehalose, histidine, and calcium chloride. Albumin-Free formulations of Factor VIII are believed to require an amorphous matrix for the protein in the presence of large amounts of crystallized excipients to provide an elegant cake structure. Hence, Factor VIII has been formulated in high salt formulations, high glycine, and high mannitol formulations where these excipients are purposely crystallized out during the freezing phase of lyophilization by annealing the frozen matrix to the eutectic crystallization temperature of the crystallizing. A small amount of stabilizer, preferably or trehalose, is added to the formulation for protection and stabilization of the Factor VIII in the amorphous matrix of the lyophile.

SUMMARY

The albumin-free formulation of Factor VIII in a high salt, low sucrose and low glycine matrix is a lyophilized formulation that is a pharmaceutically-acceptable drug product suitable for treating hemophilia. The addition of small amounts of glycine to the formulation surprisingly resulted in good cake structure, high recovery of FVIII activity across lyophilization, and a stability profile that was similar to the formulation containing only sucrose in high salt matrix. The addition of the small amount of glycine (3-6 mg/ml, 40-80 mM) also surprising increased the primary glass transition temperature of the frozen matrix from −45° C. to −38° C. making the formulation easier to lyophilize. Since Factor WIT favors environments with high NaCl, the sucrose/glycine frozen matrix also appears to have higher NaCl content than the sucrose matrix alone. This surprising observation may also favor enhanced stability for a lyophilized Factor VIII formulation.

The invention provides a stable, albumin-free lyophilized FVIII preparation, comprising, when reconstituted in water up to about 300 to 320 mM NaCl, up to about 50 mM buffer, preferably histidine, capable of providing a pH of about 6.5 to about 7.5, up to about 1-5 mM $CaCl_2$, up to about 10-25 mM of a disaccharide, preferably sucrose or trehalose, up to about 20 to 80 mM glycine and up to about 50-2000 IU Factor VIII per milliliter. In addition, the composition may contain a non-ionic surfactant, preferably TWEEN®-20 (polysorbate 20) or TWEEN®-80 (polysorbate 80) in an amount above the critical micelle concentration, preferably at concentration between 50-150 ppm. The preferred FVIII is B-domain deleted rFVIII with a specific activity between 8,000 and 15,000 IU per milligram as determined by the chromogenic assay.

The preferred stable, albumin-free lyophilized recombinant FVIII preparation, when reconstituted in water, is composed of, up to about 308 mM NaCl, up to about 50 mM of histidine, capable of providing a pH of 6.5 to 7.5, up to about 1 to 5 mM $CaCl_2$, up to about 10-25 mM of sucrose or trehalose, up to about 40-80 mM Glycine and up to about 50-3000 IU B Domain Deleted recombinant Factor VIII.

DETAILED DESCRIPTION

Objectives

The objective of this work is to provide a pharmaceutically acceptable formulation of Factor VIII that is stable in the absence of albumin. FVIII is preferably recombinant FVIII (rFVIII), most preferably B Domain Deleted rFVIII (BDDrFVIII). We found that the use of a sugar, preferably a disaccharide, most preferably sucrose or trehalose, in combination with glycine provides such stability and provides good cake formation after lyophilization. The preferred sugar concentration is 10-25 mM.

In particular, the present invention comprises of a small amount of glycine, 20-80 mM, preferably 40-80 mM, 0.3-0.6 wt %, is added to a high ionic strength formulation comprising of around 250-400 mM NaCl, preferably 250-320 mM NaCl, most preferably 308 mM (18 mg/ml). Surprising the addition of glycine appears to prevent some of the NaCl from crystallizing out during freezing and hence provide a stabilizing amorphous salt/sucrose/glycine matrix for FVIII.

The glycine addition to the formulation increases the primary glass transition temperature of the formulation matrix by almost 7° C., hence making the formulation easier to lyophilize at a higher shelf temperature during primary drying. The small amount of glycine also results in generating a good cake structure for this formulation and does not comprise the overall stability of the lyophilized product. Both the NaCl/sucrose and NaCl/sucrose/glycine formulations have similar stability profiles.

Other components may be added such as a buffer, capable of providing a pH of about 6.5 to about 7.5. A preferred buffer is histidine. Also a nonionic surfactant, such as polysorbate 80 (TWEEN® 80) or polysorbate 20 (TWEEN® 20), at concentrations above the critical micelle concentration, may be added. In addition, $CaCl_2$ in a concentration of 1-5 mM may be added to preferred preparations.

SPECIFIC EMBODIMENTS

Example 1

Figure 1:
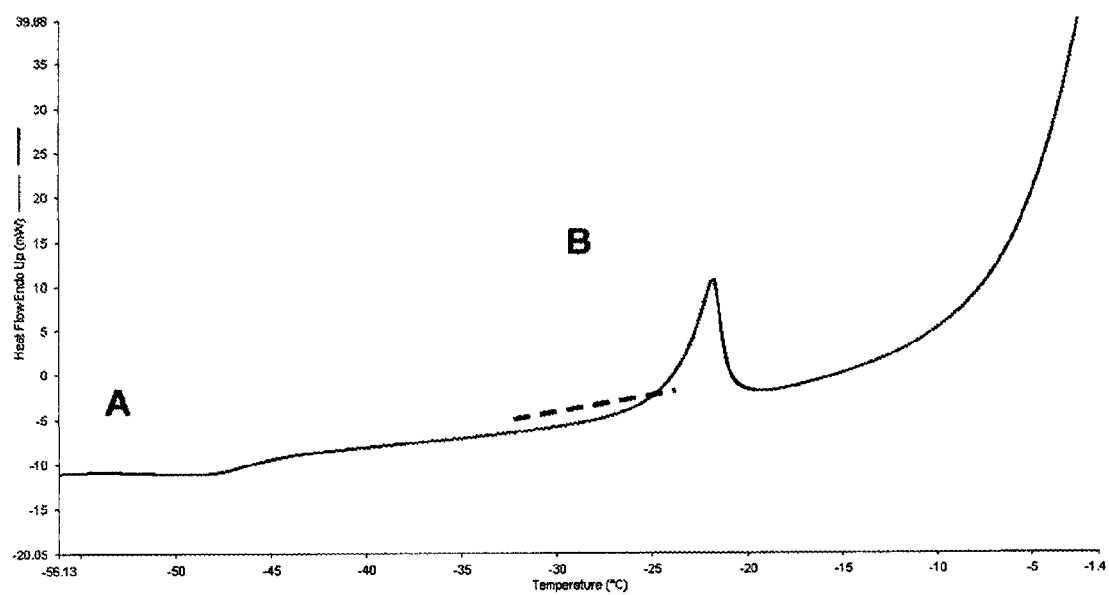
FIG. 1 shows a warming thermogram obtained with Differential Scanning calorimetry (DSC) of a FVIII formulation composed of 18 mg/ml NaCl and 6 mg/ml sucrose with no glycine. The y axis is Heat Flow (mW); and the x axis is Temperature in degrees Centigrade. Two major thermal events are indicated by "A" and "B". The primary glass transition (Tg') is indicated by "A" and has a mid-point of Tg' of −45.5° C. Event "B" shows the eutectic melting of crystallized NaCl in the frozen matrix at −21.8° C. The heat of enthalpy of NaCl melting was 12 Joules Per gram (J/g).
Figure 2:
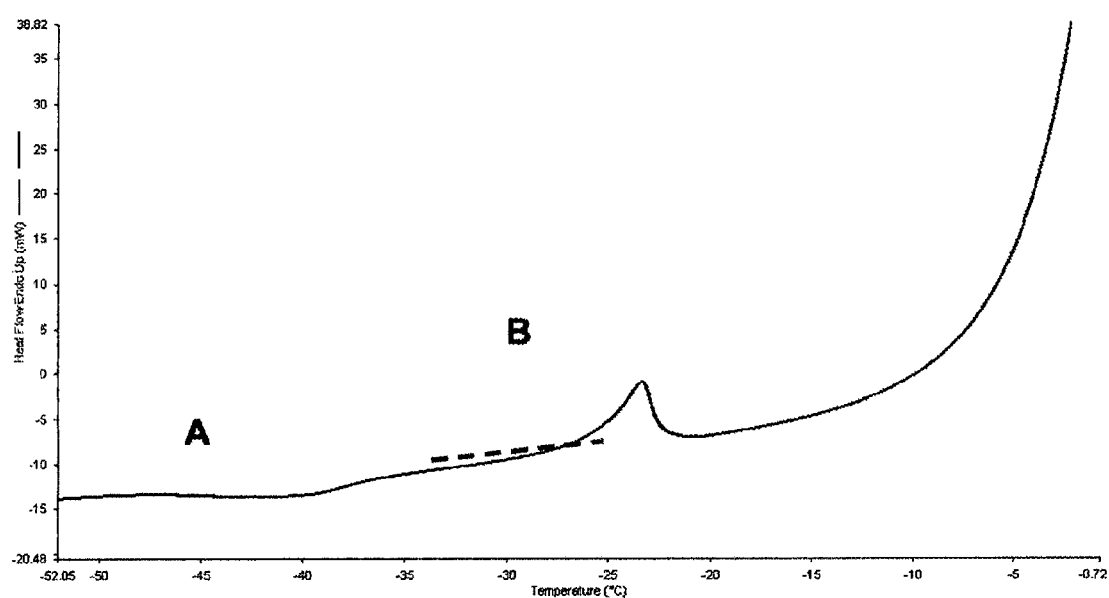
FIG. 2 shows a warming thermogram Obtained with Differential Scanning calorimetry (DSC) of a FVIII formulation composed of 18 mg/ml NaCl and 6 mg/ml sucrose with 6 mg/ml glycine. The y axis is Heat Flow (mW); and the x axis is Temperature in degrees Centigrade. Two major thermal events are indicated by "A" and "B". The primary glass transition (Tg') is indicated by "A" and has a mid-point of Tg' of −38.3° C. Event "B" shows the eutectic melting of crystallized NaCl in the frozen matrix at −23.4° C. The heat of enthalpy of NaCl melting was 6.4 J/g.

The thermal properties of FVIII formulations in high ionic strength containing sucrose alone and in sucrose/glycine were characterized by Differential Scanning calorimetry (DSC). As shown in FIGS. 1 and 2, the addition of low amounts of glycine surprising resulted in increasing the primary glass transition of the formulation matrix by almost 7° C. The amount of crystallized NaCl in the sucrose/glycine matrix was almost half the crystallization in the sucrose alone formulation as shown by the enthalpic energy of eutectic melting of NaCl at −21 to −23° C. These results strongly suggest that sucrose/glycine matrix contains significantly higher amounts of amorphous NaCl.

Example 2

A multivariate Design Of Experiments (DOE) was performed on FVIII formulations evaluating the effects of multiple excipients on the lyophilized formulations. Parameters such as recovery of FVIII activity across lyophilization, appearance of cake structure, and stability under accelerated conditions (8 weeks storage at 40° C.) were evaluated.

Figure 3:
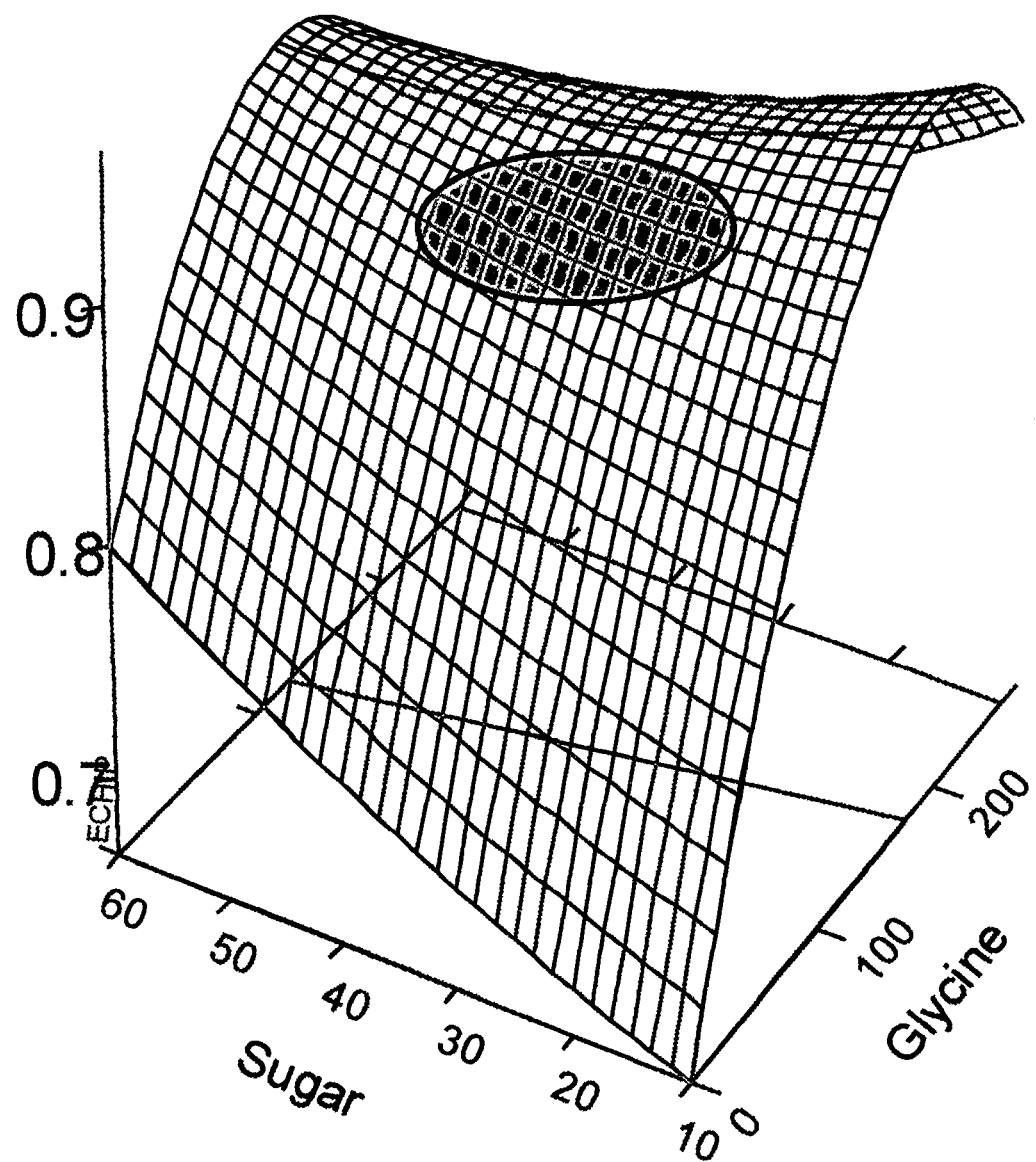
FIG. 3 is a response-surface graph on the Recovery of Factor VIII activity across lyophilization. The response-surface curve shows the interaction of low amounts of sucrose and glycine in high salt formulation of FVIII resulting in high recovery across freeze-drying as denoted by the circle. The concentration of sugar (sucrose) in mM is on the x axis; the concentration of glycine in mM is on the y axis; the vertical z axis is the amount of recovery over the initial amount of Factor VIII activity (IU/ml). The response-surface represents all formulations that contain 208 mM NaCl and no mannitol. The shaded area represents the design space with high recovery across lyophilization.
Figure 4:
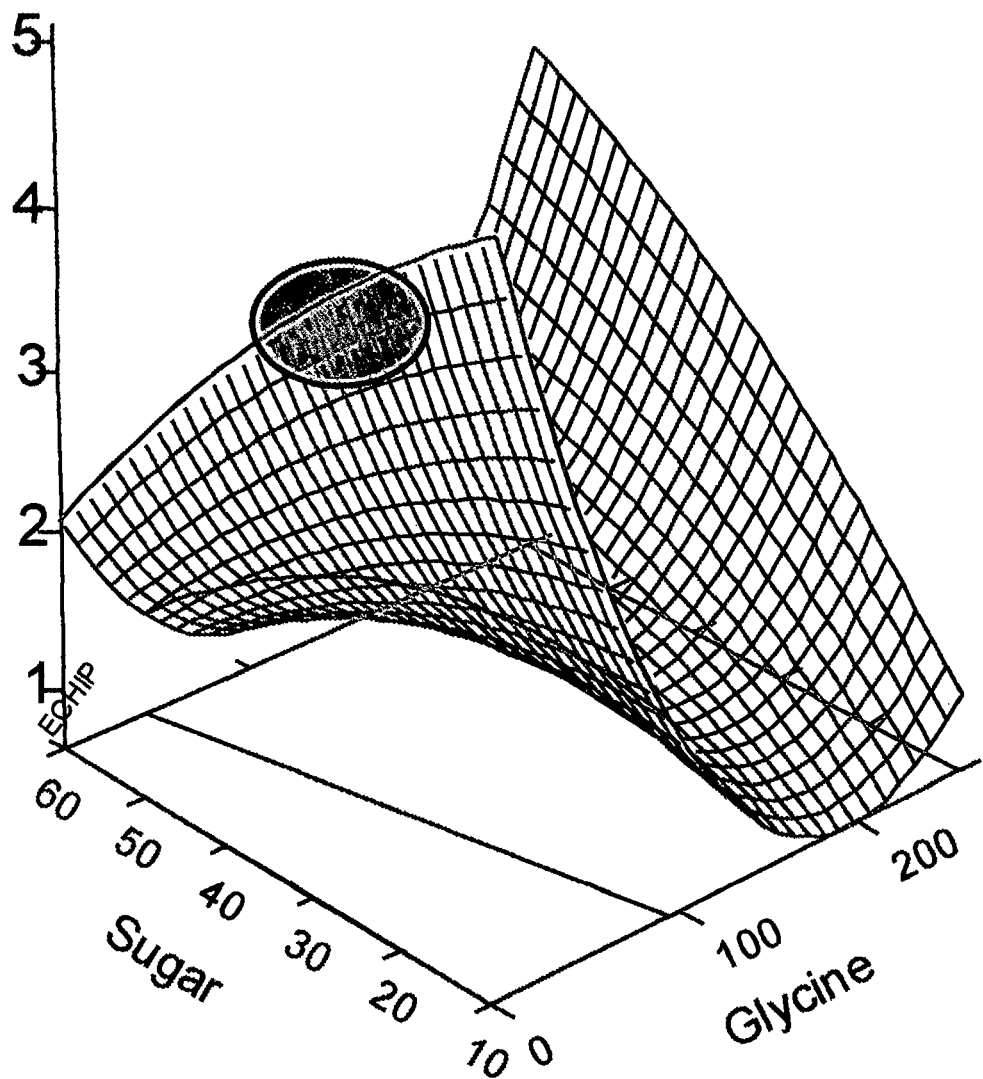
FIG. 4 is a response-surface graph on the Cake Appearance following lyophilization. The concentration of sugar (sucrose) in mM is on the x axis; the concentration of glycine in mM is on the y axis. The vertical z axis is the qualitative appearance of cake structure, where 5 is excellent cake appearance and 1 is poor/collapsed cake appearance. The response-surface represents all formulations that contain 248 mM NaCl and no mannitol. The complex response surface shows the interactions of low amounts of sucrose and glycine in high salt formulation of FVIII resulting in good cake structure across freeze-drying as denoted by the shaded circle.
Figure 5:
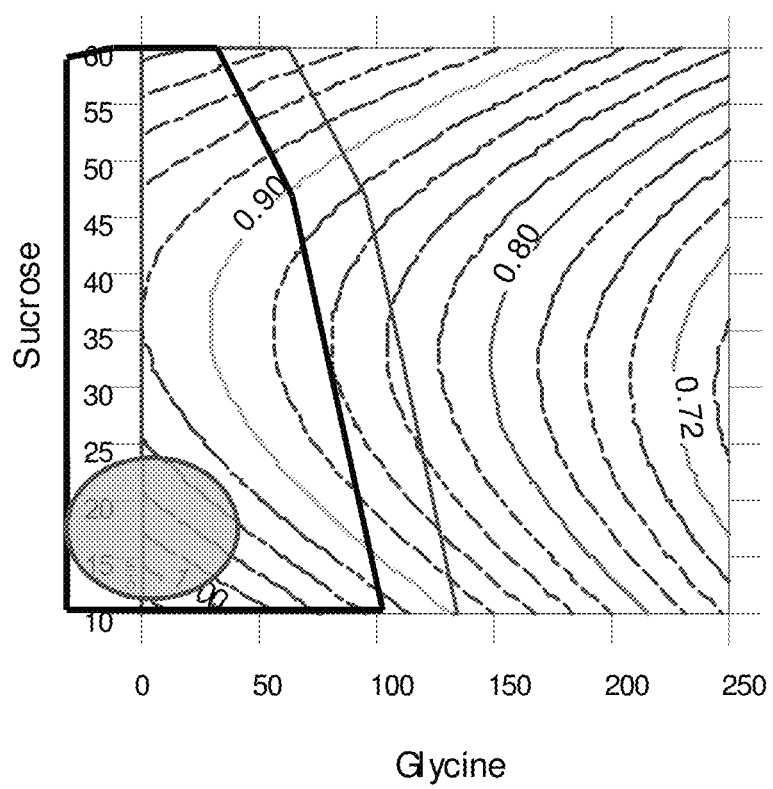
FIG. 5 is a contour surface graph showing the interaction of low amounts of sucrose and glycine in high salt formulation of FVIII resulting in excellent stability of FVIII activity of greater than 90% of initial activity as denoted by the shaded circle. The response-surface represents all formulations that contain 228 mM NaCl and no mannitol. The concentration of glycine in mM is on the x axis; the concentration of sugar (sucrose) in mM is on the y axis. The contour lines represent the amount of ratio of Factor VIII activity (IU/ml) activity over the initial value (at time=zero). For example, 0.90 contour line represents 90% of initial potency after storage for 8 weeks at 40° C. The area within the bold line represents the actual design space of the formulations tested and the area outside represents the predicted values from the statistical analysis of the Design of Experiment trials.

FIGS. 3-5 show the DOE analysis of these formulations. The shaded areas on the graphs in FIG. 3 show areas of high recovery across lyophilization. Good cake structure was evaluated by a qualitative ranking system from 1-5, where 5 is a good solid cake and 1 is a collapsed cake. FIG. 4 shows the DOE results of the cake structure. Excellent cake structure was observed in the shaded circle where the formulations had low amounts of sucrose and glycine at salt concentrations. FIG. 5 shows the stability data where good stability was observed in formulations with low amounts of sucrose and glycine as illustrated by the shaded circle area on the graph.

Together the results show that formulations with low amounts of sucrose and glycine gave high recoveries across lyophilization, good cake structure, and excellent stability under accelerated temperatures (40° C.) over an eight week storage period.

Example 3

Figure 6:
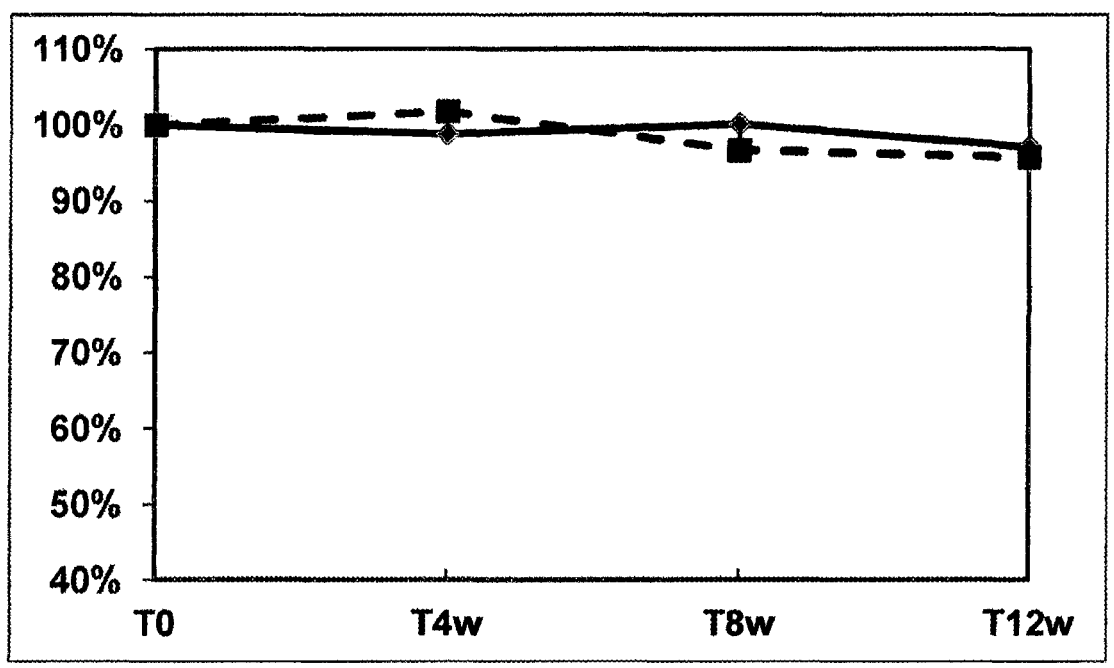
FIG. 6 shows the stability of formulations of FVIII composed of 308 mM NaCl and low amounts of sucrose (6 mg/ml) (line with solid diamonds) and low amounts of sucrose (6 mg/ml) and glycine (3 mg/ml) (dashed line with solid squares) over 12 weeks of storage at 25° C. The storage time at 25° C. is shown on the x axis in weeks; the percent of initial FVIII activity in shown on the y axis.
Figure 7:
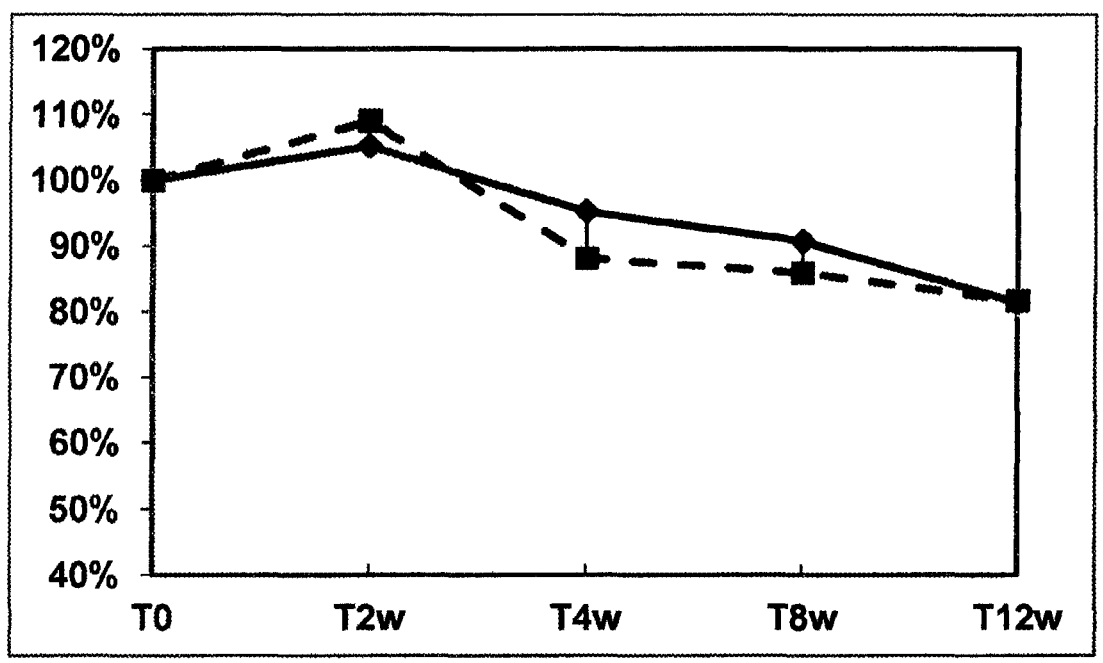
FIG. 7 shows the stability of formulations of FVIII composed of 308 mM NaCl and low amounts of sucrose (6 mg/ml) (line with solid diamonds) and low amounts of sucrose (6 mg/ml) and glycine (3 mg/ml) (dashed line with solid squares) over 12 weeks of storage at 40° C. The storage time at 40° C. is shown on the x axis in weeks; the percent of initial FVIII activity in shown on the y axis.

Stability of FVIII in formulations of high salt (308 mM) and low amounts of sucrose (18 mM) (solid line in FIGS. 6 and 7) or in low amounts of sucrose (6 mg/ml, 18 mM) and glycine (3 mg/ml, 80 mM) (dashed line in FIGS. 6 and 7) were evaluated over 12 weeks of storage at 2-8° C. and at accelerated temperature of 40° C. FIG. 6 shows the 2-8° C. stability data and FIG. 7 shows the 40° C. stability data. Both formulations show similar stability profiles for both formulations over the 12 weeks of the study.

Example 4

Figure 8:
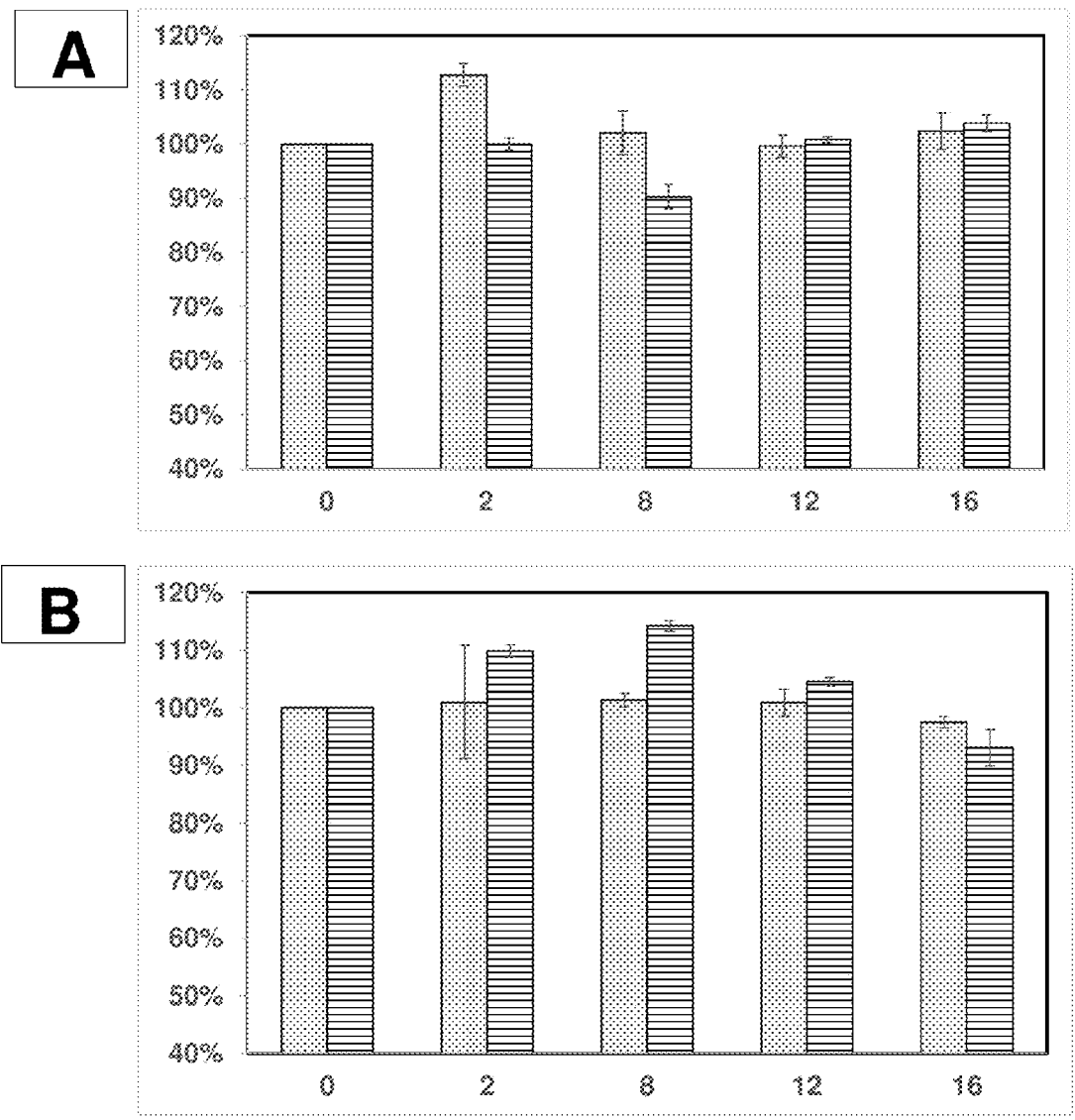
FIG. 8 shows the stability of sucrose and sucrose/glycine formulations of lyophilized B Domain Deleted recombinant FVIII (BDDrFVIII) preparations at two different dosage forms, when tested for storage at 5° C. Graph A (top) shows the 2000 IU Dosage Form; Graph B shows the 250 IU Dosage Form. The dotted bars are formulations of FVIII composed of 308 mM NaCl and low amounts of sucrose (6 mg/ml) and the bars with horizontal lines are formulations of FVIII composed of 308 mM NaCl and low amounts of sucrose (6 mg/ml) and glycine (3 mg/ml). The x axis shows storage time in weeks at 5° C.; the y axis shows potency (% of initial). The error bars are standard deviations from triplicate vials.
Figure 9:
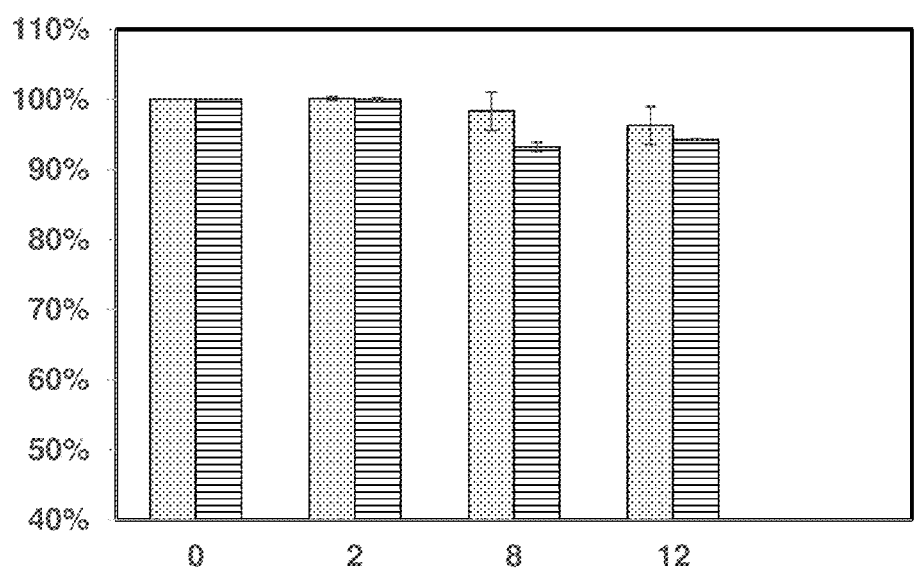
FIG. 9 shows the stability of sucrose and sucrose/glycine formulations of lyophilized B domain deleted rFVIII preparations at two different dosage forms, when tested for storage at 25° C. Graph A (top) shows the 2000 IU Dosage Form; Graph B shows the 250 IU Dosage Form. The dotted bars are formulations of FVIII composed of 308 mM NaCl and low amounts of sucrose (6 mg/ml) and the bars with horizontal lines are formulations of FVIII composed of 308 mM NaCl and low amounts of sucrose (6 mg/ml) and glycine (3 mg/ml). The x axis shows storage time in weeks at 25° C.; the y axis shows potency (% of initial). The error bars are standard deviations from triplicate vials.
Figure 9:
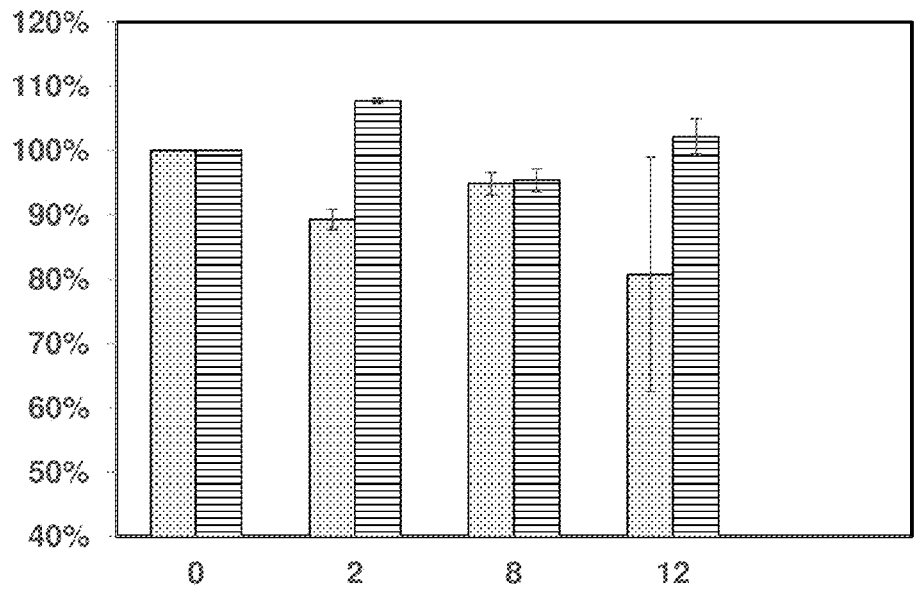
Figure 10:
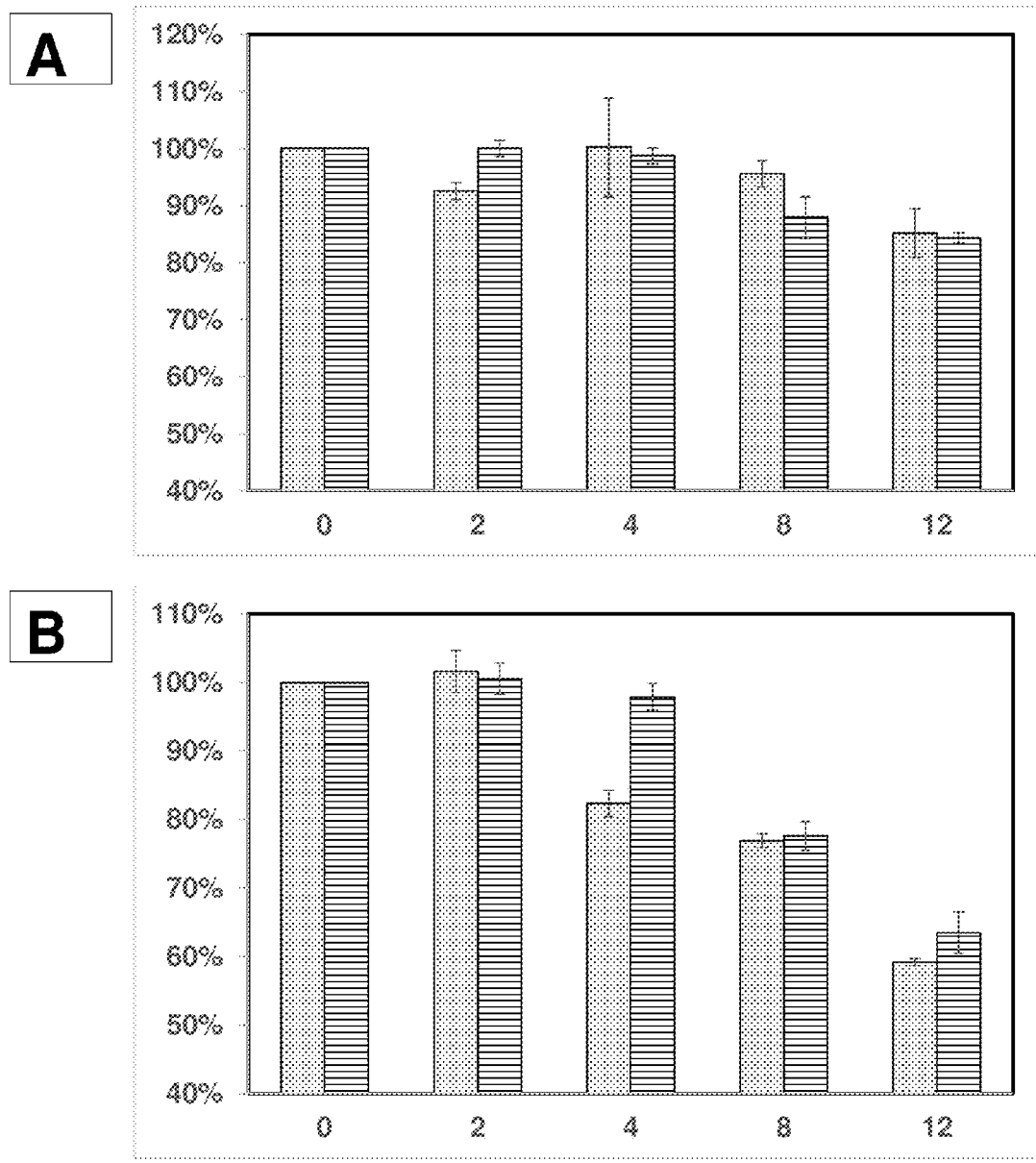
FIG. 10 shows the stability of sucrose and sucrose/glycine formulations of lyophilized B domain deleted rFVIII preparations at two different dosage forms, when tested for storage at accelerated temperature of 40° C. Graph A (top) shows the 2000 IU Dosage Form; Graph B shows the 250 IU Dosage Form. The dotted bars are formulations of FVIII composed of 308 mM NaCl and low amounts of sucrose (6 mg/ml) and the bars with horizontal lines are formulations of FVIII composed of 308 mM NaCl and low amounts of sucrose (6 mg/ml) and glycine (3 mg/ml). The x axis shows storage time in weeks at 40° C.; the y axis shows potency (% of initial). The error bars are standard deviations from triplicate vials.

Stability of FVIII in formulations of at a high dosage form of 2000 IU/vial and low dosage form at 250 IU/vial at different storage conditions are shown in FIGS. 8, 9, and 10. Two formulations containing high salt (308 mM) and low amounts of sucrose (18 mM) (bars with dots in FIGS. 8, 9 and 10) or high salt (308 mM) and in low amounts of sucrose (6 mg/ml, 18 mM) and glycine (3 mg/ml, 80 mM) (bars with horizontal lines in FIGS. 8, 9 and 10) were evaluated over 16 weeks of storage at 2-8° C. and over 12 weeks at accelerated temperatures of 25° C. and 40° C. Both formulations show similar stability profiles for both formulations over the 12 weeks of the study.

The above examples are intended to illustrate the invention and it is thought variations will occur to those skilled in the art. Accordingly, it is intended that the scope of the invention should be limited only by the claims below.

The invention claimed is:

1. A stable, albumin-free lyophilized Factor VIII (FVIII) composition comprising NaCl, buffer, $CaCl_2$, disaccharide, glycine, and FVIII, wherein the composition comprises, when reconstituted in water,
   250-400 mM NaCl,
   up to 50 mM buffer that provides a pH of 6.5-7.5,
   1-5 mM $CaCl_2$,
   10-25 mM disaccharide,
   20-80 mM glycine, and
   50-3,000 IU Factor VIII per milliliter.

2. The composition according to claim 1, wherein the buffer is histidine.

3. The composition according to claim 2, wherein the composition further comprises a non-ionic surfactant in an amount above the critical micelle concentration.

4. The composition according to claim 3, wherein the non-ionic surfactant is selected from the group consisting of polysorbate 80 and polysorbate 20.

5. The composition according to claim 1, wherein the disaccharide is sucrose or trehalose.

6. The composition according to claim 1, wherein the FVIII is recombinant FVIII (rFVIII).

7. The composition according to claim 6, wherein the rFVIII is B-domain deleted protein having a specific activity between 8,000-15,000 IU/mg.

8. The composition according to claim 1, wherein:
   the concentration of NaCl is 250-320 mM,
   the concentration of buffer is up to 50 mM,
   the concentration of $CaCl_2$ is 1-5 mM,
   the concentration of disaccharide is 10-25 mM,
   the concentration of glycine is 20-80 mM, and
   the concentration of FVIII is 50-3,000 IU FVIII per milliliter.

9. A stable, albumin-free lyophilized recombinant Factor VIII composition comprising NaCl, buffer, $CaCl_2$, disaccharide, glycine, and FVIII, wherein the composition comprises, when reconstituted in water,
   308 mM NaCl,
   up to 50 mM histidine that provides a pH of 6.5 to 7.5, 1-5 mM $CaCl_2$,
   10-25 mM sucrose or trehalose,
   40-80 mM glycine, and
   50-3,900 IU B-domain deleted recombinant Factor VIII.

10. A method of treating hemophilia in a subject in need thereof, the method comprising administering to the subject the composition of claim 1, thereby treating hemophilia in the subject.

11. The method according to claim 10, wherein the buffer in the composition is histidine.

12. The method according to claim 11, wherein the composition further comprises a non-ionic surfactant in an amount above the critical micelle concentration.

13. The method according to claim 12, wherein the non-ionic surfactant is selected from the group consisting of polysorbate 80 and polysorbate 20.

14. The method according to claim 10, wherein the disaccharide in the composition is sucrose or trehalose.

15. The method according to claim 10, wherein the FVIII is recombinant FVIII.

16. The method according to claim 10, wherein the rFVIII is B-domain deleted protein having a specific activity between 8,000-15,000 IU/mg.

17. A method of treating hemophilia in a subject in need thereof, the method comprising administering to the subject the composition of claim 9, thereby treating hemophilia in the subject.

18. A method of preparing the composition of claim 1, the method comprising combining NaCl, buffer, $CaCl_2$, disaccharide, glycine, and FVIII in the absence of albumin.

19. A method of preparing the composition of claim 9, the method comprising combining NaCl, buffer, $CaCl_2$, disaccharide, glycine, and FVIII in the absence of albumin.

* * * * *